(12) United States Patent
Baker (10) Patent No.: US 8,054,458 B2
(45) Date of Patent: Nov. 8, 2011

(54) OPTICAL DEVICE FOR DETECTING LIVE INSECT INFESTATION

(76) Inventor: Roger C. Baker, Austin, TX (US)

( * ) Notice: Subject to any disclaimer, the term of this patent is extended or adjusted under 35 U.S.C. 154(b) by 516 days.

(21) Appl. No.: 12/282,850

(22) PCT Filed: Mar. 21, 2007

(86) PCT No.: PCT/US2007/064494
§ 371 (c)(1),
(2), (4) Date: Sep. 12, 2008

(87) PCT Pub. No.: WO2007/109710
PCT Pub. Date: Sep. 27, 2007

(65) Prior Publication Data
US 2009/0097019 A1   Apr. 16, 2009

Related U.S. Application Data (60) Provisional application No. 60/743,618, filed on Mar. 21, 2006.

(51) Int. Cl.
*G01N 21/00* (2006.01)
*G01J 5/02* (2006.01)
(52) U.S. Cl. ............... 356/237.1; 250/341.7; 250/338.1
(58) Field of Classification Search .... 356/237.1–237.5, 356/239.1–239.8; 250/338.1, 358.1, 341.7
See application file for complete search history.

(56) References Cited

U.S. PATENT DOCUMENTS

| | | | |
|---|---|---|---|
| 4,572,666 A | | 2/1986 | Satake |
| 4,794,549 A | * | 12/1988 | Van Albert et al. ............. 73/866 |
| 4,937,555 A | * | 6/1990 | Litzkow et al. ............... 340/540 |
| 4,941,356 A | * | 7/1990 | Pallaske .......................... 73/587 |
| 5,245,188 A | | 9/1993 | Satake et al. |
| 5,594,654 A | * | 1/1997 | Shuman et al. ............... 700/213 |
| 5,616,845 A | * | 4/1997 | Hickling et al. ................ 73/584 |
| 5,646,404 A | * | 7/1997 | Litzkow et al. ............ 250/338.1 |

(Continued)

FOREIGN PATENT DOCUMENTS
GB   2277587   *   2/1994

(Continued)

OTHER PUBLICATIONS

Perez-Mendoza et al. "Detection of Stored-Grain Insect Infestation in Wheat Transported in Railroad Hopper-Cars" J. Econ. Entoma, 97(4)1474-1483 (2004).

(Continued)

*Primary Examiner* — Hoa Pham
(74) *Attorney, Agent, or Firm* — Meyertons, Hood, Kivlin, Kowert & Goetzel, P.C.; Eric B. Meyertons (57) ABSTRACT

The disclosure relates to a detection device for detecting movement of a live insect located within a seed or grain. The device may include a light source with a masking arrangement to block stray light. It may also include a detection region sized to contain at least one seed. Finally, the device may include a detection instrument able to detect changes in light from the light source caused by movement of an insect within the seed. The disclosure also relates to a method of detecting an insect in a seed. First, one may pass light through the seed. Then one may detect light passed through the seed and, based on the light passed through the seed, determine whether or not an insect within the seed is moving.

39 Claims, 9 Drawing Sheets

U.S. PATENT DOCUMENTS

| | | | |
|---|---|---|---|
| 7,496,228 B2 * | 2/2009 | Landwehr et al. | 382/170 |
| 2002/0185605 A1 * | 12/2002 | Shuman et al. | 250/341.7 |
| 2003/0048927 A1 | 3/2003 | Sato et al. | |

FOREIGN PATENT DOCUMENTS

| | | |
|---|---|---|
| JP | 03-140845 | 6/1991 |
| JP | 2815633 | 8/1998 |

OTHER PUBLICATIONS

International Preliminary Report on Patentability for PCT Application No. PCT/US2007/064494.

International Search Report and Written Opinion for PCT/US2007/064494, Dated Oct. 19, 2007 (12 PP.).

Laopongsit, et al. "Early detection of insect infestation in stored grain based on head space analysis of volatile compounds." 10th International Working conference on Stored Product Protection, Julilus-Kuhn-Archiv, 2010, pp. 999-1004.

Maghirang et al. "Automated Detection of Single Wheat Kernels Containing Live or Dead Insects Using Near-Infrared Reflectance Spectroscopy", American Society of Agricultrual Engineers, 2003, vol. 46, pp. 1277-1282.

* cited by examiner

OPTICAL DEVICE FOR DETECTING LIVE INSECT INFESTATION

RELATED APPLICATION

This application claims the benefit of provisional patent application entitled "Optical Device for Detecting Live Insect Infestation of Grain," U.S. Application Ser. No. 60/743,618 filed 21 Mar. 2006.

TECHNICAL FIELD

The present disclosure, in accordance with specific example embodiments, generally relates to optically detecting the presence of live insects in seeds and grain. In some embodiments it relates to detecting and monitoring the movement of insects developing within individual seeds. In some embodiments, it relates to detecting the microscopic movements of weevils in grains of wheat.

BACKGROUND

In the United States alone, grain loss due to insect damage has been estimated to exceed about 1 billion dollars per year. The grain industry hopes to discover some means of detecting and accurately quantifying hidden insect or other infestation in grain.

For example, wheat stored in bulk is prone to develop a nearly invisible internal infestation by the wheat weevil, *Sitophilus granarius*, and closely related insects. The weevils tend to propagate in zones of wheat processing equipment that trap and hold grain long enough for these insects to thrive and spread. The solution to this infestation problem seems to be mainly a combination of the prevention and the early detection of infestation.

Because the life cycle of such insects may be as little as about one month, these grain weevils can multiply quickly enough to ruin large shipments of stored grain. Many methods have been proposed to detect this type of internal infestation. Detection of hidden infestation is quite important to the grain trading industry, but the various proposed and existing methods of detecting hidden wheat weevil infestation all have certain drawbacks.

Many methods of detecting hidden infestation have been proposed and used. These methods include the staining of material used to plug the egg holes, density separations, crushing kernels in ninhdrin impregnated paper, detection of carbon dioxide and uric acid, insect antibodies, x-rays, the audible detection of faint sounds emitted by internal larvae, NMR, insect antibody detection, etc. Most of these methods are quite complex or are tedious or lack necessary sensitivity. The antibody method, in particular, is quite sensitive but is too complex and takes too long to be widely used at the inspection site.

Grain industry brokers seek sensitive, accurate tests for hidden infestation of grain before purchase or transportation for later sale. Failure to detect infestation may lead to destruction of the entire lot of grain. Any inspection method that depends on visible assessment of damage will often miss internal insect infestation. Most of the commonly used methods, such as the insect-damaged kernal (IDK) test, are inaccurate and imprecise, often dependent on subjective judgments by human inspectors.

The US government promulgates standards based on visible inspection of the grain for insects and insect damage. For example, more than two live insects per kilogram of wheat or more than 32 infested grains in a more closely inspected 100 gram grain sample are the grading criteria in condemning wheat for human food use.

Each of the known methods of detecting wheat weevil infestations has certain drawbacks. Cracking and flotation is not very accurate, as indicated by the wide scatter in the data generated by different labs. Insect antibody detection is very sensitive and also accurate, but it is not easily adapted for rapid field use by unskilled workers. The same is the case with X-ray detection, which requires both expensive equipment and skilled operators. One proposed method uses passive near infrared spectra measurements; however, this method requires expensive equipment.

Almost all of the techniques currently employed for insect detection both fail to discriminate between live and dead insects and to detect internal insect infestation. It has been found that most of the commonly used methods of detecting infestation are inaccurate. (B. Brader, et al., A comparison of screening methods for insect contamination in wheat,*J. Stored Products Res.*: 38, pp. 75-86 (2002); G. E. Russell, Evaluation of four analytical methods to detect weevils in wheat; Granary weevil, *Sitophilus granarius* (L) in soft white wheat, *J. Food. Protect.*: 51, pp. 547-553 (1988).) In one study, while only 4% of wheat samples from 79 elevators were found to be infested by normal inspection, 16% of the samples were found to be infested after they were incubated from 4-6 weeks. (C. L. Storey, et al., Insect infestations in wheat and corn exported from the United States, *J. Econ. Entomol.*: 75, pp. 827-832 (1982).) Hidden infestation, then, is a common and important problem.

SUMMARY

Due to field conditions appropriate for grain inspections, one would ideally prefer to have an automatic wheat weevil detection instrument that could be used by an unskilled operator to detect and quantify the level of insect infestation in a grain sample weighing about 50 grams within about 15 minutes. An automated wheat weevil detection system would provide the potential to sample grain more accurately than alternative techniques used. Teachings of the present disclosure may be satisfactorily used for a wide variety of seeds and other items subject to insect infestation, of which wheat grains are an example, but not meant to limit the scope of this disclosure.

One embodiment of the disclosure relates to a detection device. The device may include a light source with a masking arrangement to block stray light. It may also include a detection region sized to contain at least one seed. Finally, the device may include a detection instrument able to detect changes in light from the light source caused by movement of an insect within the seed.

Another embodiment relates to an automated detection device. The device may include a rotatable horizontal cylinder having a plurality of slots sized to hold a single seed and a plurality of shelves each configured to separate a single seed from a pool of seeds and position the single seed within one of the plurality of slots. The device may include a feed pan located near the cylinder configured to contain the pool of seeds. The device may include a light source positioned to shine through one or more of the plurality of slots at a given rotational position. The device may include a detector positioned to detect light shining from the light source through the one or more slots and any seed positioned in the one or more slots.

Another embodiment relates to an inspection device. The device may include a pan including a bottom. The bottom may include an opening sized to hold an item to be inspected. The device may also include an emitter positioned to shine light through the opening. The device may include a detector positioned to detect light shining from the emitter through the opening and any item positioned in the opening.

The disclosure also relates, in one embodiment, to a method of detecting an insect in a seed. First, one may pass light through the seed. Then one may detect light passed through the grain and) based on the light passed through the grain, determine whether or not an insect within the grain is moving.

BRIEF DESCRIPTION OF THE FIGURES

A more complete understanding of this disclosure may be acquired by referring to the following description taken in combination with FIGS. 1-9.

While the present disclosure is susceptible to various modifications and alternative forms, specific example embodiments have been shown in the figures and are herein described in more detail. It should be understood, however, that the description of specific example embodiments is not intended to limit the disclosure to the particular forms disclosed, but on the contrary, this disclosure is to cover all modifications and equivalents as defined by the appended claims.

DETAILED DESCRIPTION

The present disclosure, according to specific example embodiments, generally relates to optically detecting and monitoring the microscopic movements of weevils developing within individual grains of a grain product. More specifically, it relates to weevil detection instruments and techniques. At a very general level, embodiments of the disclosure take advantage of the fact that weevil movement may be detected by shining a light through a wheat grain. In many cases, weevil movements may cause fluctuations in the transmitted light. If no weevil is present, then little or no fluctuation is observed beyond the inherent light sensor noise. The teachings of the present disclosure, however, may be applied to a wide variety of infestation and inspection devices and methods. In general, any item subject to infestation by insects or other moving things may be inspected using the teachings of the present disclosure.

In many embodiments, the difference in fluctuations based on the presence or absence of a weevil may be so pronounced that they may be detected even with instruments insensitive to small fluctuations. In such embodiments, the chance of false positives may be low. The chance of false negatives may be higher, particularly in grains with small weevils or that are improperly positioned, but may be mitigated by using instruments sensitive to small fluctuations. False negatives may also be reduced by warming the grain, which often causes the weevil to move more. Thermostatic warming of the interior of the instrument may also serve to stabilize any electronic circuitry contained within.

Although wheat grains are used in exemplary embodiments throughout this disclosure, it will be understood to one skilled in the art that the techniques and instruments may be adaptable for use with other objects subject to internal insect infestation, particularly those with similar optical properties. Further, although weevils have been used as the exemplary organism throughout this disclosure, it will also be understood that other insects that live within and move inside of a seed or grain at some stage in their life cycles may also be detectable using similar methods and techniques. For instance, one skilled in the art may use the teachings of the present disclosure to inspect any seed, nuts, fruits, cereal grains, and/or other items subject to internal insect infestation.

For example, various organisms such as callosobructus are known to burrow into foodstuffs (e.g., peas and beans) and develop stealthily. Teachings in accordance with the present disclosure may be used to inspect for such infestations.

Additionally, while visible light and near infrared light are used in example embodiments, other embodiments of the disclosure may use other forms of light, such as longer wavelengths of infrared light. Any wavelength of light able to pass through an infested item so that movement of a weevil larvae may be detected may be suitable. It will be understood by one skilled in the art that detectors may additionally be varied, particularly based on the wavelength of light selected and its intensity. For example, some reports have measured light passing through "a full-size, unskinned honeydew melon" with a diode laser using 2f detection of the 910 nm carbohydrate band and the water peak at 958 nm (Michael Lang, "Diodes Storm the Tunable Laser Ranks", *Photonics Tech Briefs*, http://www.ptbmagazine.com/articles/diodes0199).

When wheat grains are strongly illuminated from below with a strong white light passing though a light masking hole, larval movements can sometimes be seen under a low power microscope. The movements of wheat weevils may resemble shadows moving around inside the grain. Various techniques and instruments for optical detection of weevils in wheat grains may be developed based on these observations. Detection of movement may detect live insects only. For storage of wheat and other grains, it is live insects that are of primary concern. Given the life cycle characteristics of insects such as granary weevils, even a small initial infestation can very rapidly cause significant problems.

Embodiments of the present disclosure may include a light source with a masking arrangement to block stray light. They may also include a detection region in which one or more wheat grains may be placed. Finally, the instruments may include one or more detectors, which may be able to detect minute changes in light from the source caused by weevil movement inside of a wheat grain. Such an instrument may be used by placing a wheat grain in the detection region, illuminating it using the light source, detecting light using one or more detectors, and then using the detected light to determine whether the wheat grain contains a live weevil larva.

In one embodiment, a method may include transmitting a strong beam of near infrared LED light through a wheat grain, with the stray light being blocked by a masking arrangement. This method is based on the fact that wheat grains transmit an useful amount of both yellow and longer light wavelengths, extending well into the infrared.

Slight movements of the larvae inside a seed may result in the fluctuation in the intensity of the transmitted light as detected by an electronic photo sensor. The fluctuating electronic signal may be amplified to detect weevil larvae or other infestations. In addition, in some embodiments, sensitivity to larval movements may be increased by measuring a slight imbalance in the transmitted and scattered light detected by two separate photosensors, these typically being phototransistors or photodiodes. Dual sensors may tend to cancel out various sources of drift. In addition the larval movements within the seed may tend to decrease the light intensity signal into one sensor while simultaneously increasing the signal into the other. The sensor imbalance may be easily detected by electronic instrumentation known in the art. In embodiments including a single detector for each inspection, a large area photodiode may provide satisfactory results.

Figure 1:
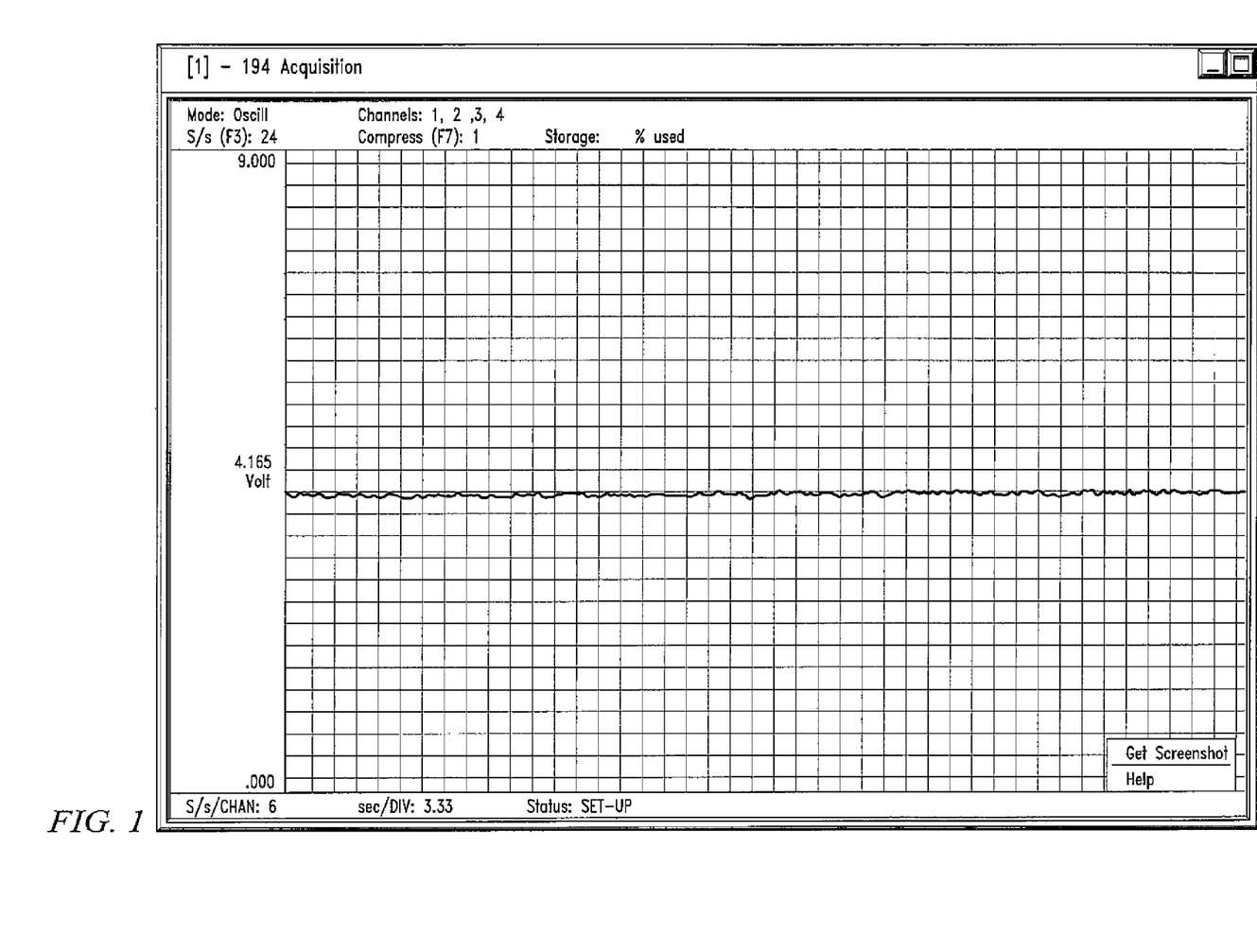
FIG. 1 is a chart generated by a system embodying the teachings of the present disclosure. The chart shows the base noise level from an uninfected wheat grain recorded with a serial port DATQ A/ID converter and associated software. This and other charts in the present disclosure show 3.33 seconds per horizontal division with a vertical scale that is arbitrary, but consistent in all charts.

FIG. 1 is a chart generated by a system embodying the teachings of the present disclosure. The chart shows the base noise level from an uninfected wheat grain recorded with a serial port DATQ A/D converter and associated software. This and other charts in the present disclosure show 3.33 seconds per horizontal division with a vertical scale that is arbitrary, but consistent in all charts.

Figure 2:
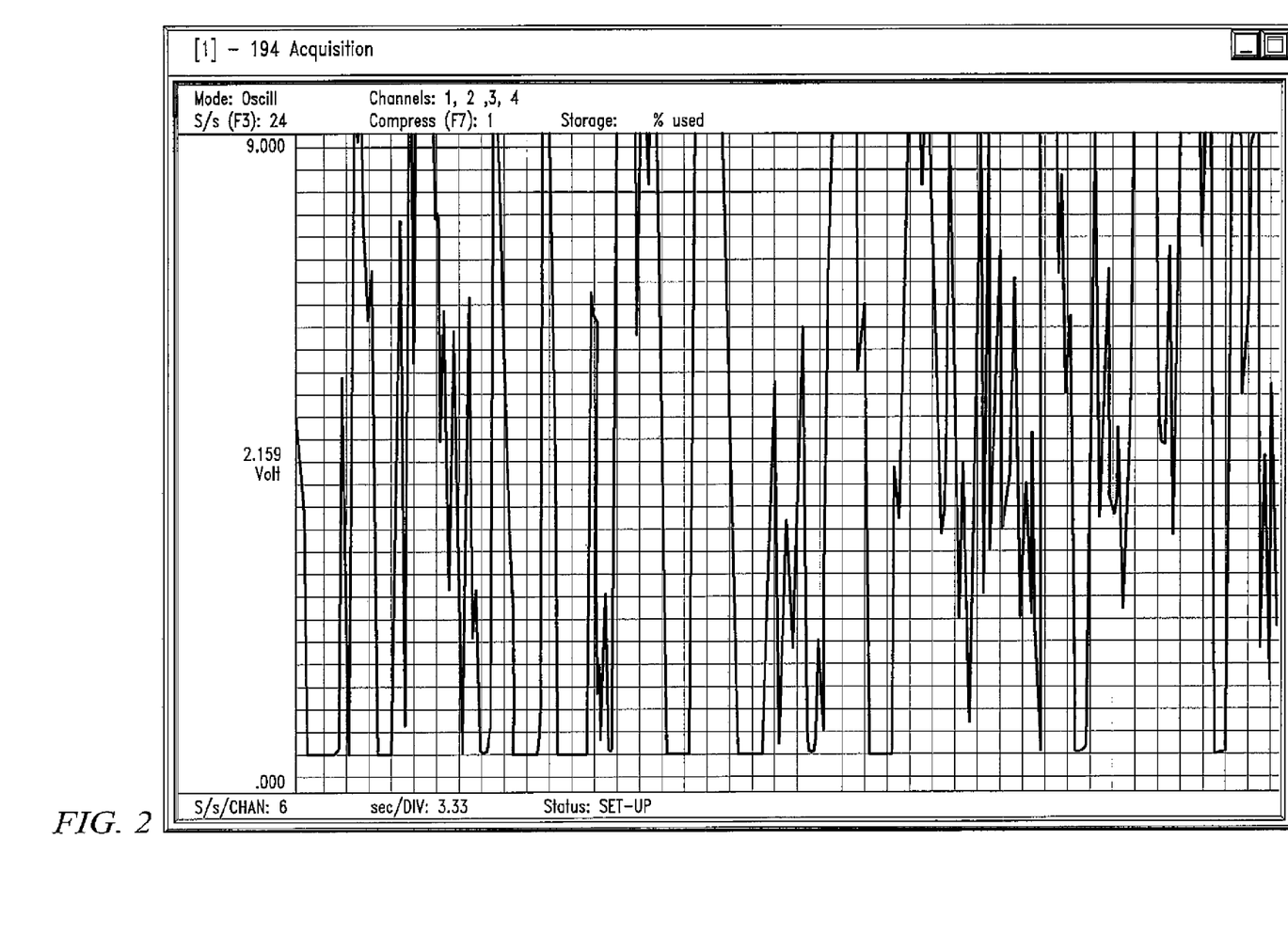
FIG. 2 is a chart showing the more than full scale signal generated by a late-stage wheat weevil larva that has not yet emerged from an infested wheat grain. Scale and conditions are the same as in FIG. 1.

FIG. 2 is a chart showing the more than full scale signal generated by a late-stage wheat weevil larva that has not yet emerged from an infested wheat grain. Scale and conditions are the same as in FIG. 1. Systems and embodiments in accordance with the teachings of the present disclosure may take advantage of the strength of such a signal to identify infested grains.

Figure 3:
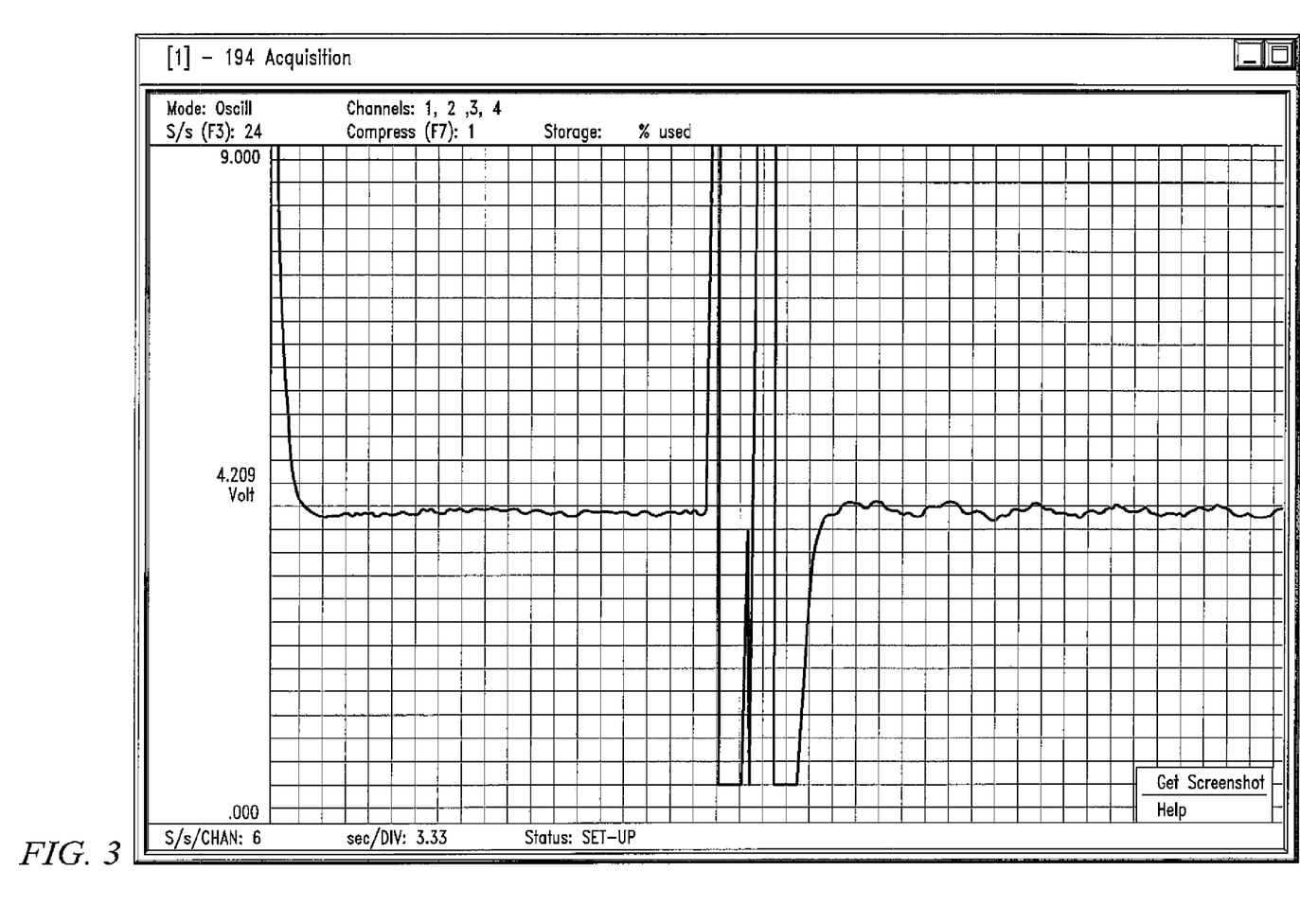
FIG. 3 is a chart showing the signal produced by a small weevil larva. The wheat grain was removed during recording, turned end over end and reintroduced before recording resumed. Signal changes based on grain condition and, in some positions, is indistinguishable from background noise. Scale and conditions are the same as in FIG. 1.

FIG. 3 is a chart showing the signal produced by a small weevil larva. The wheat grain was removed during recording, turned end over end and reintroduced before recording resumed. Signal changes based on grain condition and, in some positions, is indistinguishable from background noise. Scale and conditions are the same as in FIG. 1.

Figure 4:
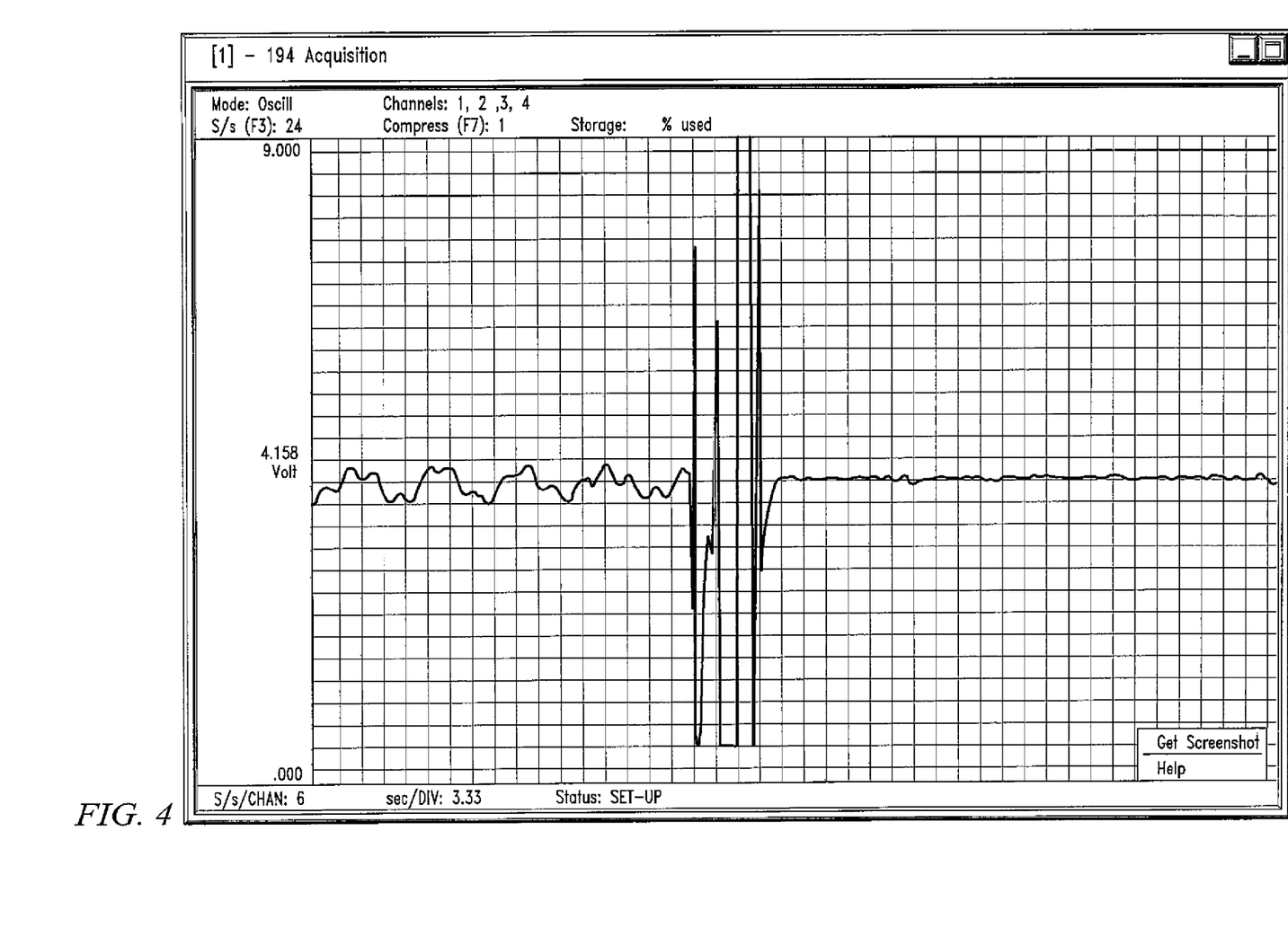
FIG. 4 is a chart produced in the same manner as FIG. 3 with the same wheat grain. In one position, the weevil movements cause slow signal changes extending above the typical noise level for infested grain.

FIG. 4 is a chart produced in the same manner as FIG. 3 with the same wheat grain. In one position, the weevil movements cause slow signal changes extending above the typical noise level for infested grain.

Figure 5A:
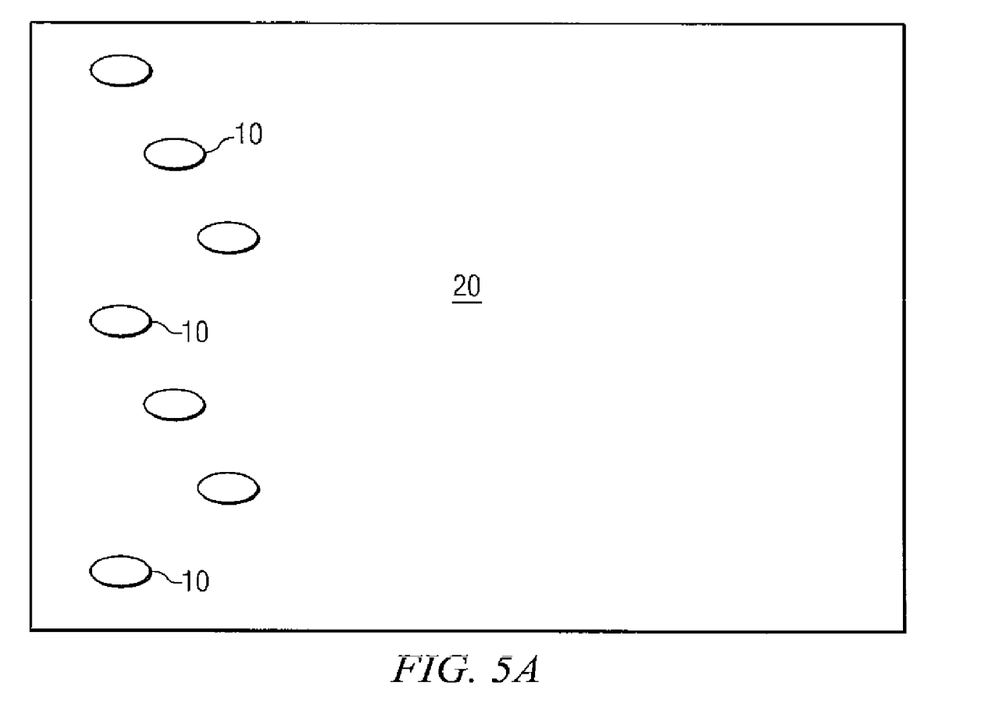
FIG. 5A is a top view of a grain container in accordance with teachings of the present disclosure.
Figure 5B:
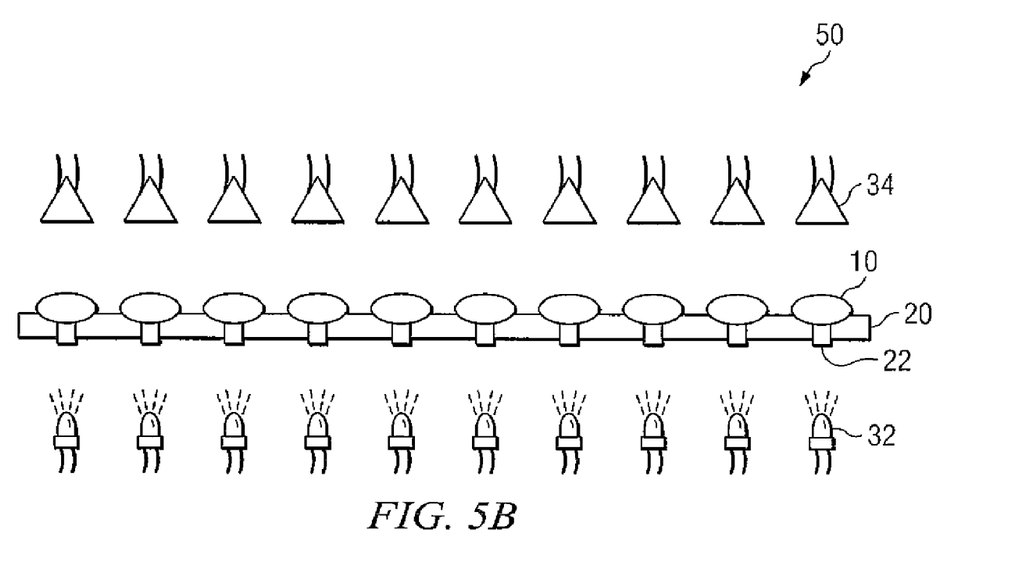
FIG. 5B is a side view of a grain container and sensor system in accordance with teachings of the present disclosure.

FIGS. 5A and 5B show a grain container and sensor system in accordance with teachings of the present disclosure. Grain container 20 and sensor system 30 may be components of system 50. System 50 may be any system generally designed to provide a detection region in which it may expose one or more grains to a light source and detect the light passing through the grain. System 50 may include grain container 20, sensor system 30, and/or any other components or devices useful in practicing the teachings of the present disclosure. System 50 may be operable to inspect grain 10 individually for a period of around a few seconds with sensor system 30 operable to measure minute changes in the transmission of light through grain 10.

FIGS. 5A and 5B also show a representation of grain 10 which may be the target of system 50. Grain 10 may include any grain, seed or other appropriate item including, but not limited to, cereal grains such as wheat grains and/or oats, legumes such as peanuts, soybeans and/or peas, and/or fruits, such as nuts (e.g., pecans, walnuts, almonds and/or cashews).

Grain container 20 may be any device or feature of system 50 generally configured to provide a detection region. In some embodiments, grain container 20 may include one or more openings 22. Opening 22 may be any feature or component of grain container 20 generally configured to hold a single grain 10 and allow sensor system 30 to access grain 10 from at least two opposing directions.

Grain container 20 may also include any other features or components configured to facilitate the handling of grain 10 or operation of sensor system 30. Grain container 20 may be fabricated of any suitable material, such as metal or plastic.

In some embodiments, prescreening grains 10 may serve to improve the results of the inspection. For example, a sample of grains 10 to be inspected may include a wide variety of sizes and shapes, not all of which may be compatible with grain container 20 or sensor system 30. In such cases, a visual inspection or a filter may serve to improve performance. For example, grains 10 may be passed through two tilted rotating concentric tubular screens. One screen may include a large mesh operable to restrict passage of grains 10 that are too large for proper inspection and a small mesh operable to restrict passage of grains 10 that are suitable for proper inspection. In such a manner, grains 10 which might not be compatible with grain container 20, openings 22 and/or sensor system 30 may be eliminated from inspection and improve the results generated.

FIG. 5A is a top view of one embodiment of grain container 20 in accordance with teachings of the present disclosure. In the view depicted by FIG. 5A, each opening 22 contains a single grain 10. In embodiments such as that depicted in FIG. 5A, a set of openings 22 may be staggered rather than aligned in a single row. Such an arrangement may serve to isolate each grain 10 and opening 22 from nearby grains 10 and openings 22 and may further serve to reduce interference between inspections.

FIG. 5B is a side view of grain container 20 and sensor system 30 in accordance with teachings of the present disclosure. FIG. 5B also shows a single grain 10 present in each opening 22 provided by grain container 20. Opening 22 may be configured to hold and/or align grain 10 and to provide access for sensor system 30 to operate from opposing sides of grain 10.

Sensor system 30 may be any component or device configured to expose grain 10 to light and detect any light passing through grain 10. In some embodiments, such as that shown in FIG. 5B, sensor system 30 may include emitter 32 and detector 34. As shown in FIG. 5B, sensor system 30 may include one emitter 32 and detector 34 for each opening 22 in grain container 20.

Emitter 32 may be any device or component operable to expose grain 10 to light. Emitter 32 may provide visible light, infrared light, and/or any other sort of light energy that is suitable for the grains and/or infesting object that is the subject of the inspection by system 50 (e.g., a light bulb, an LED, and/or an x-ray source). For example, emitter 32 may include a gallium arsenide LED operable to put out ten or more milliwatts of power at about 940 nanometers wavelength (near-infrared).

Emitter 32, whether a single emitter or an array of emitters as shown in FIG. 5B, may be disposed in proximity to grain container 20 and openings 22 so that it may tend to fully illuminate an entire grain 10 positioned in opening 22. In such embodiments, grain container 20 may be fabricated from a material chosen to provide a light masking effect. That is, grain container 20 may operate to shield grain 10 from exposure to light other than that provided by emitter 32.

Detector 34 may be any device or component operate to detect light passing through grain 10. In some embodiments, detector 34 may be chosen for maximum sensitivity to light provided by emitter 32. For example, detector 34 may include a silicon photodiode.

Detector 34 may be chosen in any size compatible with grain 10 and/or emitter 32. In some embodiments, detector 34 may include a sensitive area of about two square millimeters. Selection of the size may be useful in providing enough sensitive area to allow amplification of the light signal without adding appreciable photon counting noise. For example, a target performance may seek to measure one part per one hundred thousand change in light transmission.

In troublesome cases, such a performance goal may serve to reduce difficulties in detecting infestations. For example, if an insect larva is of detectible size but positioned toward one end of the grain and detector 34 is only sensitive over the center of the grain, the signal may be relatively weak. In another example, an insect larva may be large and well-positioned with respect to detector 34 but in a semi-hibernation stage typical of transitions between several instar stages, leading to reduced movement relative to a fully active larva.

Figure 6:
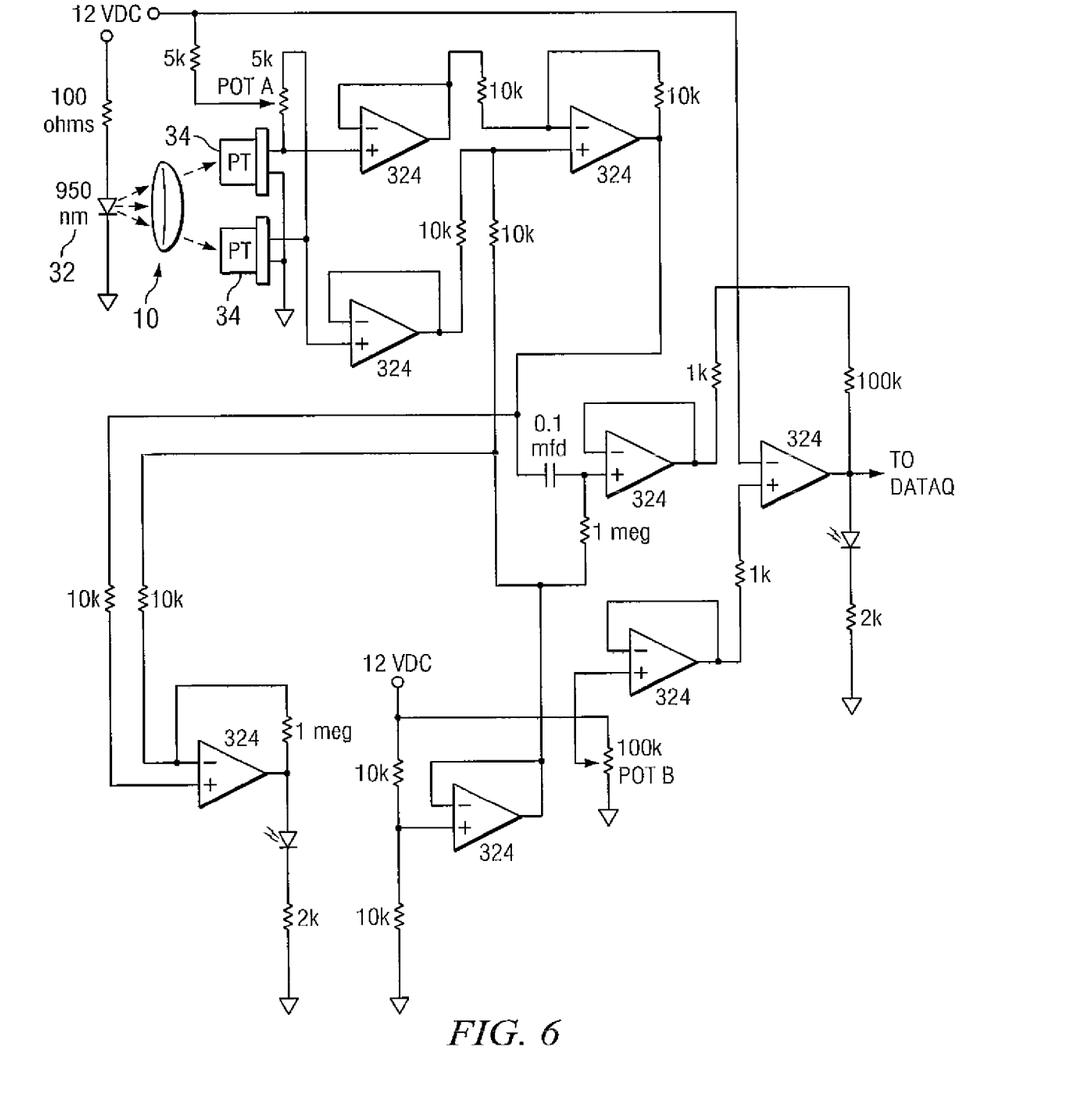
FIG. 6 is a schematic circuit of a detection and monitoring instrument in accordance with an embodiment of the present disclosure.

FIG. 6 is a schematic drawing of an electronic circuit that may be used in accordance with the present disclosure. System 50 may include any electrical circuitry or logic device generally configured to receive a signal from sensor system 30 and convey that signal to the user and/or any data collection device useful in the practice of a detection and monitoring infestation of grains. The particular circuit of FIG. 6 may serve to receive a signal from two detectors 34 and provide a single output to a data acquisition system. Persons having ordinary skill in the art will recognize that many variations of electronic circuitry or similar devices may be useful in practicing the systems or methods of the present disclosure, depending on the configuration of sensor system 30, emitter 32 and/or detector 34, as well as the particular variety of grain 10 and/or infestation of interest. The circuit depicted in FIG. 6 may be of particular use in detecting a weevil in a grain of wheat. In addition, a person having ordinary skill in the art will recognize that such an electronic circuit may be used as a single channel in a multi-channel inspection device. Such an inspection device may include as many channels as preferred to perform multiple inspections at one time. Embodiments such as those shown in FIGS. 5 and 7-9 may include multi-channel sensor circuits.

In another embodiment, an electronic circuit may include one quarter of a 324 quad op amp with a power supply of about 6 VDC or more to provide the first stage amplification for a photodiode comprising detector 34. A resistor of about 100,000 to 1,000,000 ohms may be connected to the inverting input of the op amp and its output while the photodiode may be connected between the inverting output and ground of the op amp. This configuration may provide an output signal from the op amp of around 3 volts. The output signal may then be passed through a capacitor of about 0.22 mfd which may be used to block the direct current voltage component of the sensor signal. The signal coming from the capacitor may be sensitive to fluctuations rather than a baseline signal, so it may serve to detect minute movements within the grain. The voltage fluctuation component of the signal may be amplified by a factor of about 1000 to 10,000 with an instrumentation amplifier such as a Burr Brown INA126P. As one example an amplified signal may allow the system to operate with a preset infestation alarm range of below about 2 volts or above about 4 volts. Additional components known in the art may serve to measure noise bursts as root mean square AC voltage levels, or the direct signal may be analyzed by a computer and/or a user.

In some embodiments of the present disclosure, operation of the electronic circuitry may include a step to determine whether the sensor voltage is with a normal range. The normal range may be set to include those output which may indicate the presence and correct orientation of a subject item for inspection. Absence of an item may return a sensor output outside of the normal range such as an unobstructed light beam detected by the sensor. Any embodiments including a counter or counting step may, in this manner, discard any readings from the count of items inspected. In a similar manner, a low voltage signal may be discarded. For example, an analog voltage sensing circuit combined with a data switching circuit operable to perform this step is well known in the art.

Figure 7A:
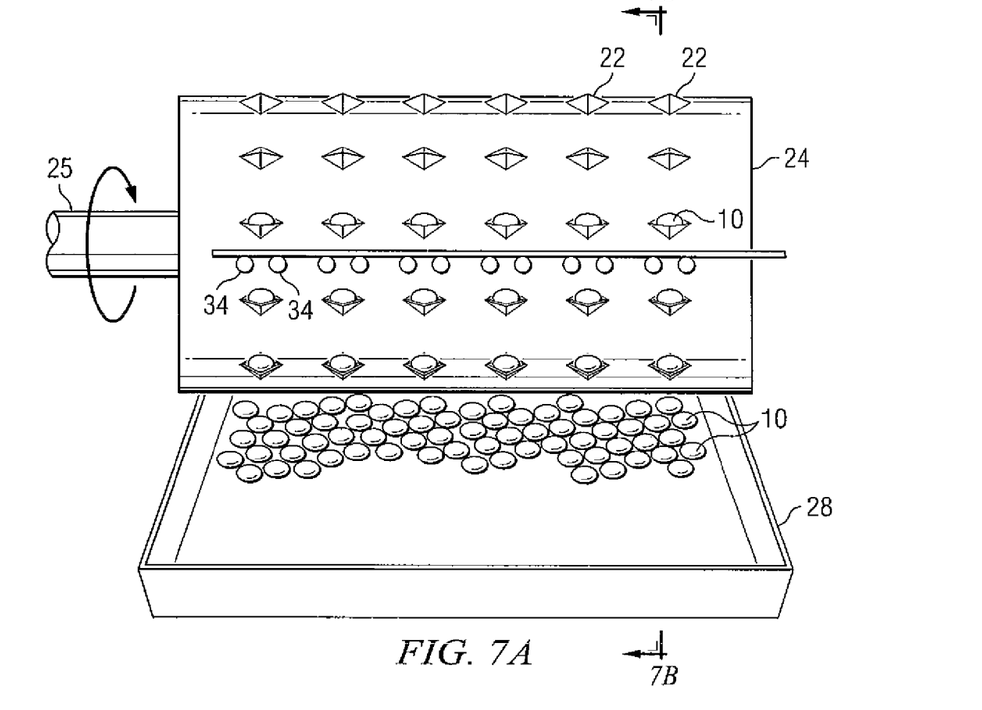
FIG. 7A illustrates a top view of a wheat infestation monitoring instrument, according to an embodiment of the present disclosure.
Figure 7B:
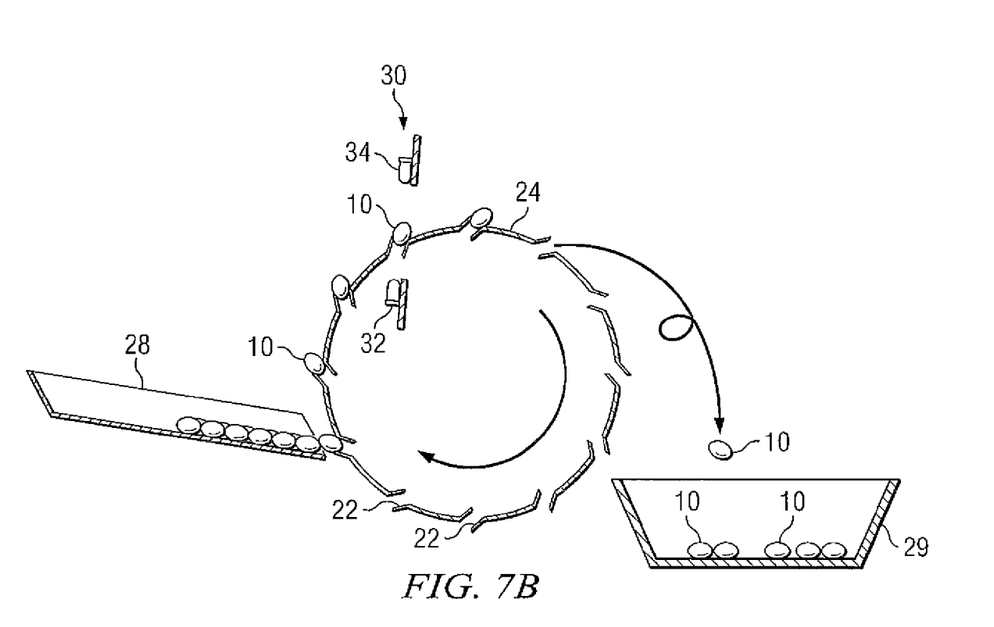
FIG. 7B illustrates a side view of a wheat infestation monitoring instrument, according to an embodiment of the present disclosure.

FIGS. 7A and 7B depict one embodiment of a wheat infestation monitoring instrument in accordance with the teachings of the present disclosure. Grain container 20 may include openings 22, cylinder 24, feed hopper 28 and discharge hopper 29. Sensor system 30 may include emitters 32 and detectors 34.

As discussed in relation to FIGS. 5A and 5B, grain container 20 may include a plurality or an array of openings 22. Each opening 22 may be configured to hold a single grain 10 so that it may be exposed to sensor system 30. In embodiments such as that depicted in FIGS. 7A and 7B, grain container 20 may include cylinder 24.

Cylinder 24 may include any array of openings 22 and components and/or features configured to move one or more openings 22 so as to expose grains 10 to sensor system 30. For example, cylinder 24 may be configured to rotate around axle 25. Cylinder 24 may include a flat sheet of material forming openings 22 around the surface of cylinder 24. In such embodiments, openings 22 may include slits formed by punching through cylinder 24. As best shown in FIG. 7B, such slits may be configured to provide a lip or edge for physical support of grain 10 when cylinder 24 rotates.

Feed hopper 28 may include any device or component of grain container 20 configured to receive and store grain 10 prior to inspection by sensor system 30. For example, feed hopper 28 may include flat sheet of material tilted to allow grain 10 to fall against cylinder 24 by the action of gravity. Feed hopper 28 may be moveable or fixed and may be of any size suitable for the desired inspection rate and/or throughput. In some embodiments, feed hopper 28 and cylinder 24 may be vibrated together along the direction of the axis of rotation of the cylinder to more reliably capture and transport the grains during the period when optical data is not being collected.

Discharge hopper 29 may include any device or component of grain container 20 configured to receive and store grain 10 after inspection by sensor system 30. For example, discharge hopper 29 may include a bin disposed below cylinder 24 so that grain 10 may fall into discharge hopper 29 as cylinder 24 rotates. Discharge hopper 28 may be moveable or fixed and may be of any size suitable for the desired inspection rate and/or throughput. In some embodiments, discharge hopper 29 may include some selectively operable device to segregate infested grains from clean grains (not expressly shown).

In embodiments such as that shown in FIGS. 7A and 7B, sensor system 30 may include emitter 32 disposed within cylinder 24. Sensor system 30 may include a pair of detectors 34 disposed to sense light passing through each opening 22 and grain 10.

A photo transistor or photodiode bridge arrangement and subsequent amplification of the imbalance between two similar phototransistors may be used to detect larval movements, with the sensitivity mainly limited by the noise level inherent to the optical sensors.

In such embodiments, each channel may have an infrared LED 22 in combination with two phototransistors 24, and electronic circuitry appropriate for filtering and balancing the analog sensor outputs (e.g., the circuitry discussed in relation to FIG. 6). Each channel may be quite inexpensive, allowing independent detection channels to be used in parallel at low cost. For example, if ten such independent detection channels are used, groups of ten or more grains may be serially examined in parallel for a given time period.

Each photo detector channel can record the amplified difference in light fluctuations from two photo sensors within a certain frequency band, expressed as an AC signal with the lower frequency of cut-off being a second or two. If the level of AC noise or noise bursts seen by the optical detectors is significantly above the background level for an uninfested grain, then the appropriate detection channel may be triggered as a positive detection event. The detected AC signal magnitude may also be digitized or recorded for further analysis.

An alternative method that may be potentially more sensitive may use an inexpensive CMOS based detector and lens arrangement to produce a magnified image of laser light transmitted though a wheat grain. The grain may be placed on top of a light masking arrangement and illuminated from underneath. A user may then detect slight shifts in the interference patterns emitted by the grain illuminated by the laser. In some embodiments, the laser may be a red laser.

The resulting light interference patterns, sometimes called speckle patterns, are fairly stable over tens of seconds in the case of uninfested wheat grains, whereas these same points of light shift when observed under magnification when a weevil is present in a wheat grain. This results from slight changes of the light transmission characteristics of wheat grains due to internal larval movements. This embodiment of a detection arrangement provides that the interference pattern is relatively insensitive to the optical focus of the objective lens and shifts in interference patterns tend to be sensitive to very slight changes in optical transmission, and are similar in this way to a very high contrast optical transmission image. Thus this approach is sensitive and offers a workable alternative to amplification of the light level detected by one or more photo sensors.

The weak IR light scattered from an uninfested grain may be noisy when using high signal amplification. This "grain noise" may set an inherent background signal that can mask small or weak larval movements. However, in practice, under optimum conditions, the amplified light signals from infested grains may rapidly fluctuate over several orders of magnitude compared to the background signal from an inert, uninfested grain. For this reason, the signal fluctuations from an actively infested grain may be easily distinguished from that of all uninfested grain, with essentially no false positives.

False negatives may result from a period of larval inactivity or bad optical detection due to non-optimum grain orientation. However, in the case of some embodiments in accordance with the present disclosure, the systems may be used to sample a statistically relevant portion of a large quantity of wheat grains. Because the systems may generate very few false positives, and the false negative error rate will tend to be constant from sample to sample, the resulting infestation data may be analyzed and corrected by well-known statistical methods. Methods of determining the true rate of false positives and false negatives, such as more careful screening and verification with alternative methods for a small sample of wheat grains, are readily determined by a person having ordinary skill in the art. Methods adapted from other mechanical or electronic food testing or manufacturing quality testing, all of which focus on statistical results for samples having many individual units to be tested, may be particularly well-suited for use with the present disclosure.

For example, some representative data, such as a light transmission signal, may be recorded electronically. This data may then be plotted in a chart. Grains emitting optical signal fluctuations above the expected background noise characteristic of uninfested grains may trigger a counter. Counter and chart data collection and analysis systems may be used in conjunction or independently.

Because false positive signals may be practically absent, depending on the noise cutoff level chosen, the infested grains may be counted. In addition, the signals may be saved using a computer or alternative data acquisition and/or storage device that may record the intensity of activity related to the size of the larva, as well as the incidence of infestation.

More rapid automated handling systems may also be developed. So long as the seed remains between the light source and a detector for an amount of time sufficient for a given percentage of weevil larvae, resulting in an acceptable number of false negatives, to move, then the system should be suitable. Automated detection systems may also be designed to meet the needs of those testing seeds. For example, they may be hand-held or readily portable without substantial risk of damage. Automated handling systems may also include a computational or a memory device able to record test results. Such systems may also include reporting features, particularly features to avoid falsified results, such as automatic wireless reporting of the production of authenticated reports.

In other embodiments, the photosensors used may be shifted into a position between two adjacent items to be inspected, which may decrease the cost of the device, and/or improve its detection sensitivity. In embodiments including detectors offset with respect to the inspected items, each photosensor may detect light from the ends or sides of two different items. The two measurements returned for one item may be compared to detect infestation. One might also be able to turn sensors adjacent to detected infestation signals on and off in this arrangement, resulting in lower operating costs.

FIGS. 8A-8D illustrate a side view of grain container 20 as well as part of an operating cycle of the instrument in accordance with teachings of the present disclosure. Embodiments such as that shown in FIGS. 8A-8D may be incorporated into larger systems operable to process multiple grain with whatever throughput may be desired. FIGS. 8A-8D show one embodiment of grain container 20 including flat tray 26, axle 25, support plate 27, and openings 22.

Flat tray 26 may include any expanse of material configured to contain grains 10 and allow grains 10 to slide from one portion of flat tray 26 to another. In some embodiments, flat tray 26 may include features or components configured to receive grains 10 from a hopper, feeder, and/or manual insertion. Flat tray 26 may include features or components configured to discharge grains 10 after inspection and, in some embodiments, segregate passed grains 10 from failed grains 10. Although FIGS. 9A-8D show one opening 22, other embodiments of flat tray 26 may include a row or array of openings 22 spread over any suitable area of flat tray 26.

Flat tray 26 may be pivotally mounted on axle 25. In other embodiments, flat tray may be mounted without a pivot. In embodiments including axle 25, axle 25 may be disposed in any location appropriate to allow flat tray 26 to rotate in a manner configured to impart lateral motion to any grains 10 contained in flat tray 26. Such motion may be useful for moving grains 10 from the location received into flat tray 26 to a location appropriate for inspection of grains 10. In embodiments without axle 25, rotation of flat tray 26 may include movement of a frame or other structure surrounding flat tray 26.

Figure 8A:
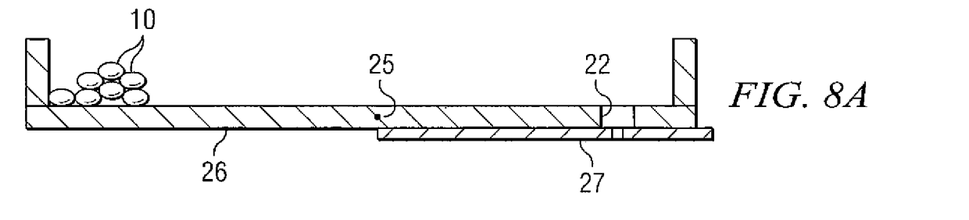
FIGS. 8A-8D illustrate a side view of a wheat infestation monitoring instrument as well as part of an operating cycle of the instrument in accordance with teachings of the present disclosure.
Figure 8B:
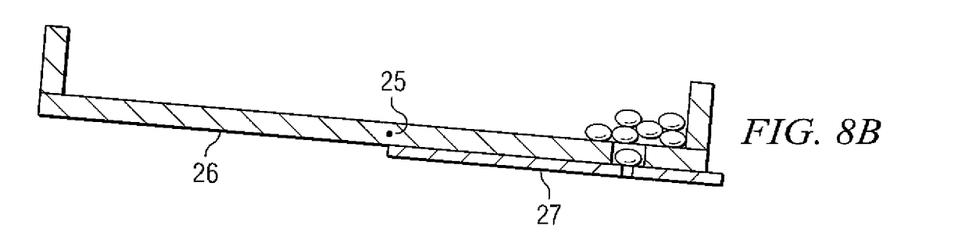
Figure 8C:
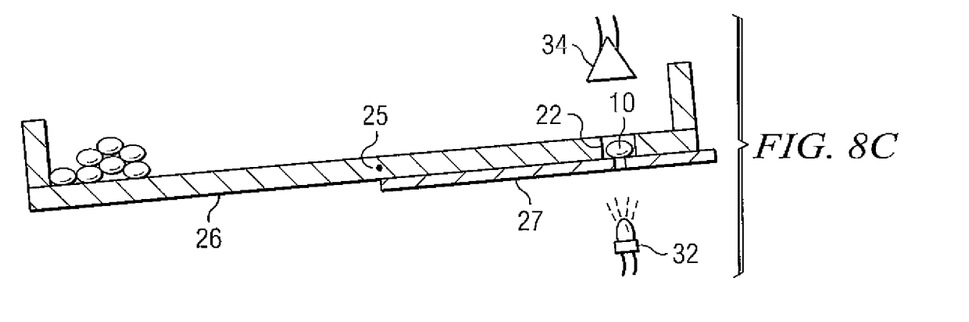
Figure 8D:
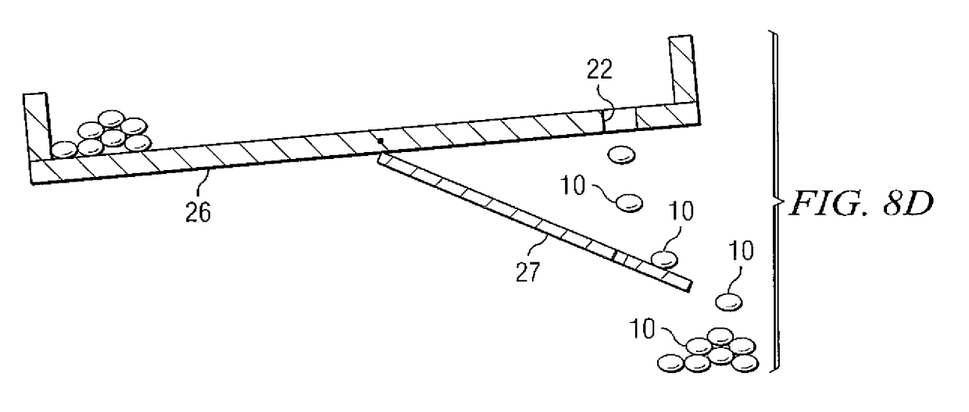

Support plate 27 may be any component or feature of grain container 20 configured to move between a first position (e.g., that shown in FIGS. 8A-8C) and a second position (e.g., that shown in FIG. 8D). Support plate 27 may be configured to restrict movement of grains 10 through openings 22 when in the first position and to allow movement of grains 10 through openings 22 when in the second position. Support plate 27 may include any features appropriate to facilitate the movement of support plate 27 between the two positions. In alternative embodiments (not expressly shown), support plate 27 may remain in a single position (e.g., that shown in FIGS. 8A-8C) and may include components or features operable to clear openings 22 so that grains 10 may move out of grain container 20 and/or flat tray 26.

FIG. 8A shows flat tray 26 in a substantially level orientation. This position may represent the beginning of an operational cycle in accordance with teachings of the present disclosure. As shown in FIG. 8A, grains 10 may be present in flat tray 26 as the result of receiving grains 10 from a feeder, a hopper, manual insertion by a user and/or any other method of delivering grains 10 to flat tray 26. In the embodiment shown in FIG. 8A, grains 10 begin at a side of flat tray 26 opposite from the location of openings 22.

FIG. 8B shows flat tray 26 in a tilted orientation such that grains 10 have slid to the opposite side of flat tray 26 than that occupied in FIG. 8A. Flat tray has rotated around axle 25 so that the portion of flat tray 26 including openings 22 is lower than other portions of flat tray 26. Such rotation may serve to allow gravity to move grains 10 toward openings 22. As shown in FIG. 8B, one grain 10 may fall into one opening 22.

FIG. 8C shows flat tray 26 back in a substantially level orientation similar to that depicted in FIG. 8A. At this point of the operational cycle depicted in FIGS. 8A-8D, grains 10 present in flat tray 26 may have slid back away from openings 22 as a result of the rotation of flat tray 26 around axle 25. At the point shown in FIG. 8C, sensor system 30 may be located relative to openings 22 so as shine light and sense light passing through openings 22 and any grain 10 located therein. As shown in FIG. 8C, sensor system 30 may include emitter 32 and detector 34 as more fully described in relation to FIG. 5B.

FIG. 8D shows one option for a discharge step which may be used in an operational cycle taking advantage of teachings of the present disclosure. As previously discussed, grain container 20 may include support plate 27 operable to move between a first position shown in FIG. 8C and a second position shown in FIG. 8D. In embodiments such as this, support plate 27 may serve to hold grains 10 in place during the inspection by sensor system 30 while in the first position. After the inspection is complete, support plate 27 may allow grains 10 to travel outside of flat tray 26 by moving and/or being moved from the first position to a second position. For example, the second position may include an angular displacement around a pivot when compared to the first position.

Figure 9:
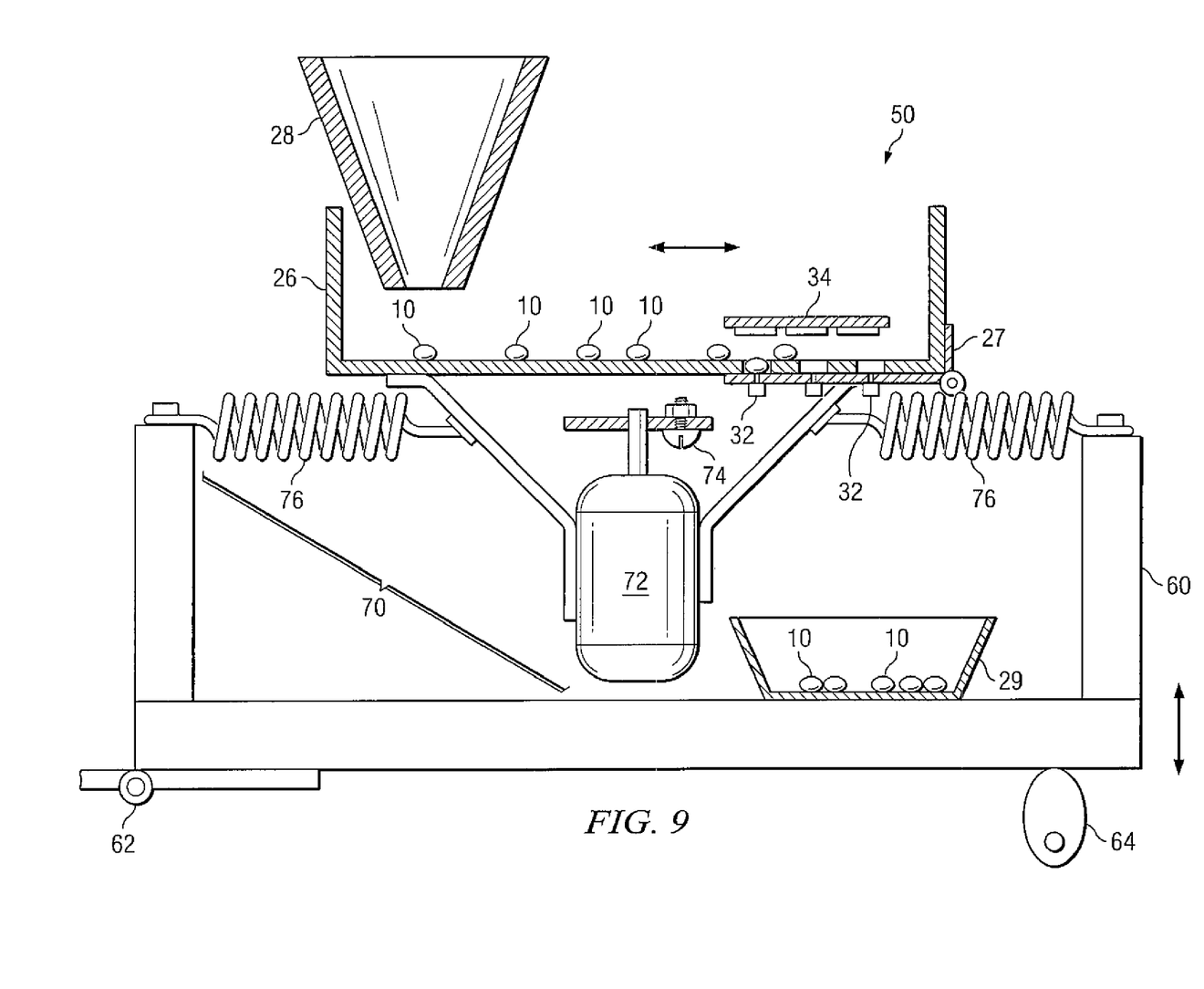
FIG. 9 illustrates a side view of a wheat infestation monitoring instrument in accordance with teachings of the present disclosure.

FIG. 9 illustrates a side view of a grain infestation monitoring instrument in accordance with teachings of the present disclosure. The embodiment depicted in FIG. 9 may be used to inspect several grains or other items at one time and may include a relatively large throughput suitable for use in a variety of applications.

Embodiments of system 50 such as that shown in FIG. 9 may include any combination of components and devices configured to expose grains 10 or other items to inspection by sensor system 30 as previously discussed. In some embodiments, system 50 may include grain container 20 configured to expose grains 10 to inspection by sensor system 30, sensor system 30 configured to expose each grain 10 to a light and sense any light passing through grain 10, frame 60 configured to house the components of system 50 and shaker 70 configured to provide vibration to grain container 20.

Grain container 20 may include flat tray 26, support plate 27, grain hopper 28 and discharge hopper 29 as discussed in relation to FIGS. 8A-8D. In embodiments such as that shown in FIG. 9, support plate 27 may serve to house emitters 32 and dispose them in close proximity to grains 10 to facilitate inspection. Sensor system may include emitters 32 and detectors 34 as discussed in relation to FIGS. 5A and 5B. As support plate 27 moves to the second position as discussed in relation to FIG. 8D, grains 10 may fall through openings 22 in flat plate 26. In some embodiments, such as that shown in FIG. 9, falling grains 10 may be collected in discharge hopper 29.

Frame 60 may include any system or device configured to support and/or house the components and features of system 50. For example, frame 60 may include structural members (e.g., u-channels and wooden boards). Frame 60 may include any system or device configured to provide motion to grain container 20. For example, frame 60 may include hinge 62 and cam 64. In such embodiments, the rotation of cam 64 may allow frame 60 to rotate around hinge 62. Such motion may serve to facilitate the motion of grains 10 in flat tray 26 from below grain hopper 28 to openings 22.

Shaker 70 may include any device or features configured to impart vibration to grain container 20 and grains 10. For example, shaker 70 may include orbital vibrator 72, offset mass 74 and springs 76. Orbital vibrator 72 may include a motor or other component operable to provide rotational energy. Offset mass 74 may be any feature or component operable to provide orbital vibration when rotated. For example, offset mass 74 may include a nut and a bolt mounted in a rotating disk mounted to the driveshaft of a motor. In embodiments including such adjustable components, the amplitude of vibration may be adjusted independently of motor speed.

In some embodiments, offset mass 74 may be mounted between orbital vibrator 72 and grain container 20. In such embodiments, orbital vibrator 72 and grain container 20 may have the same mass. In such embodiments, any vibration imparted to grain container 20 by the rotation of orbital vibrator 72 may be horizontal and lack any vertical component. Embodiments including such an arrangement may serve to be mounted to frame 60 with springs 76 without creating vibration modes of concern to a user. Other embodiments may include linear vibration without orbital vibration or shaking. In some embodiments, vibration or shaking may include a motor with an offset rotor or crank that works in concert with springs to provide lateral motion.

Techniques and instruments of the present disclosure may offer a variety of advantages compared to current detection systems and may also have other useful characteristics. For example, they may be inexpensive, capable of use by non-specialized workers, able to detect an infestation at early stages, automated, and cost-efficient. They may also provide an efficient detection time, a sensitive assay with few false positives, and an optical detection device that does not rely on chemicals which may be unsafe for food. These techniques and instruments may be useful in food quality testing, such as government testing, detection by grain industry brokers before investment, assays for determining the effectiveness of pesticides, and on-site farm product inspections.

Therefore, the present disclosure is well adapted to attain the ends and advantages mentioned as well as those that are inherent therein. While numerous changes may be made by those skilled in the art, such changes are encompassed within the spirit of this disclosure as defined by the appended claims.

The invention claimed is:

1. A detection device for detecting insects in a seed, comprising:
    one or more light sources; and
    an inspection region sized to contain one or more seeds, and configured to allow light from at one light source to pass through at least one seed and then to a detector; and
    wherein the detector is operable to detect changes in light from the seed caused by movement of an insect within the seed.

2. The device according to claim 1, further comprising an output device operable to render detected changes in light visible to a human.

3. The device according to claim 1, wherein at least one seed is wheat and the insect is a weevil larva.

4. The device according to claim 1, wherein at least one light source comprises an infrared light source.

5. The device according to claim 1, wherein at least one light source comprises a near-infrared LED.

6. The device according to claim 1, wherein at least one infrared light source comprises a laser light source.

7. The device according to claim 1, wherein at least one light source comprises a visible light source.

8. The device according to claim 7, wherein at least one light source comprises a white light source.

9. The device according to claim 1, wherein the detector comprises at least one electronic photo sensor.

10. The device according to claim 1, wherein the detector comprises two photo sensors and electronic instrumentation operable to detect an imbalance between the two sensors.

11. The device according to claim 1, wherein the detector comprises a CMOS based detector and a lens arrangement.

12. The device of claim 1, wherein the inspection region comprises a platform with an indentation.

13. The device of claim 1, wherein the inspection region is configured to inhibit light from sources other than the light sources to pass through at least one seed.

14. The device of claim 1, wherein the inspection region comprises a material, wherein the material inhibits light from sources other than the light sources to pass through at least one seed.

15. The device of claim 1, further comprising a vibrator configured to shake the inspection region to move at least one of the seeds.

16. The device of claim 1, further comprising a hopper operable to deliver at least one seeds to the inspection region.

17. The device of claim 1, further comprising a hopper operable to receive at least one seeds from the inspection region.

18. The device of claim 1, further comprising a conveyor operable to move at least one seed to the inspection region.

19. The device of claim 1, wherein the insect is alive.

20. A method of detecting an insect in a seed, comprising:
    passing light through one or more seeds;
    detecting light passed through at least one seed; and
    determining whether or not an insect is present within the seed based on the light detected from the seed.

21. The method according to claim 20, further comprising recording whether or not an insect is present within the seed.

22. The method according to claim 20, further comprising repeating the steps for a statistically significant number of seeds from an amount of seeds.

23. The method according to claim 20, wherein passing light through at least one seed comprises passing infrared light through the seed.

24. The method according to claim 20, wherein passing light through at least one seed comprises passing light from an LED through the seed.

25. The method according to claim 20, wherein passing the light through at least one seed comprises passing light from a laser through the seed.

26. The method according to claim 20, wherein passing light through at least one seed comprises passing visible light through the seed.

27. The method according to claim 20, wherein passing the light through at least one seed comprises passing white light through the seed.

28. The method according to claim 20, wherein detecting light passed through at least one seed comprises detecting shifts in interference patterns in the light.

29. The method according to claim 20, further comprising automatically performing all steps.

30. The method according to claim 20, further comprising comparing the light detected to a preset normal range of light detected and rejecting data outside the normal range.

31. The method according to claim 20, further comprising warming at least one seed.

32. The method according to claim 20, further comprising screening at least one seed to select for size prior to passing light through the seed.

33. The method of claim 20, further comprising shielding the seed from exposure to light from other sources than the passing light.

34. The method of claim 20, determining whether or not an insect is present within the seed based on the light detected from the seed comprises assessing a property of the detected light.

35. The method of claim 20, further comprising vibrating at least one seed.

36. The method of claim 20, wherein the insect is alive.

37. The method of claim 20, wherein the insect is a live wheat weevil.

38. The method of claim 20, further comprising assessing fluctuations in the light detected from the seed.

39. The method of claim 20, further comprising providing one or more seeds to the light prior to passing the light through at least one seed.

* * * * *